United States Patent [19]

Mito et al.

[11] Patent Number: 4,482,966
[45] Date of Patent: Nov. 13, 1984

[54] DETECTOR FOR CHROMATOGRAPHS

[75] Inventors: Yasuhiro Mito; Hideo Iwasaki, both of Kyoto, Japan

[73] Assignee: Shimadzu Corporation, Kyoto, Japan

[21] Appl. No.: 347,756

[22] Filed: Feb. 10, 1982

[30] Foreign Application Priority Data

Feb. 23, 1981 [JP] Japan .................................. 56-25996

[51] Int. Cl.$^3$ .............................................. G06G 7/75
[52] U.S. Cl. .................................... 364/498; 364/497; 73/23.1
[58] Field of Search ............... 364/496, 497, 498, 499, 364/555, 579, 500, 501, 571, 573, 577, 173; 73/23, 23.1

[56] References Cited

U.S. PATENT DOCUMENTS 3,691,364 9/1972 Baba et al. ........................... 364/497
4,236,894 12/1980 Summervold ....................... 364/497
4,374,424 2/1983 Coustre ............................... 364/497

Primary Examiner—Raulfe B. Zache
Assistant Examiner—Dale M. Shaw
Attorney, Agent, or Firm—Griffin, Branigan & Butler

[57] ABSTRACT

Spectrum images of chromatograph column effluent are formed on a photodiode array (7). The photodiode array (7) is scanned to produce plural detection data for predetermined plural wavelengths. The data are analytically processed and recorded to provide data ratios wherein the numerators are processed data from individual wavelengths, and the denominator in each of the ratios is the square root of the sum of the square of the processed data for the individual wavelengths. A plot of ratios versus time provides a curve which indicates completeness of chromatographic separation.

7 Claims, 11 Drawing Figures

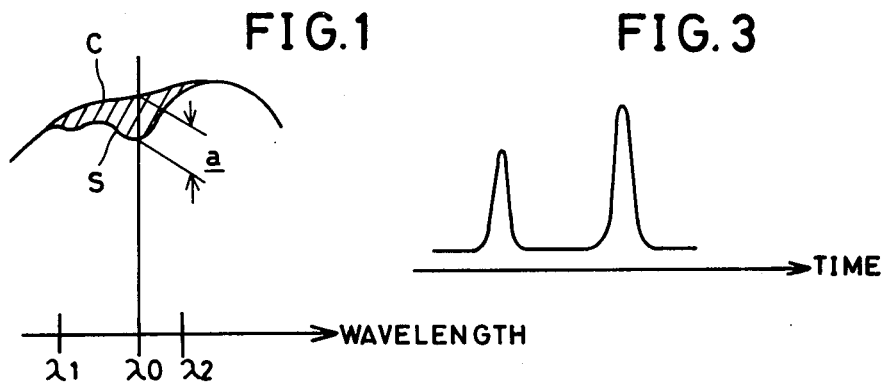
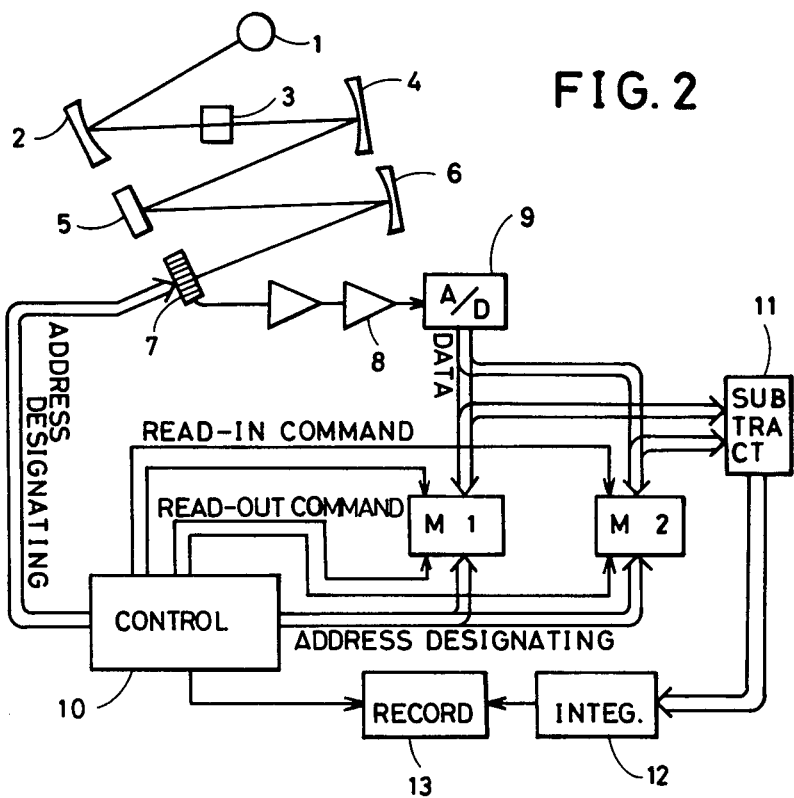

FIG. 4
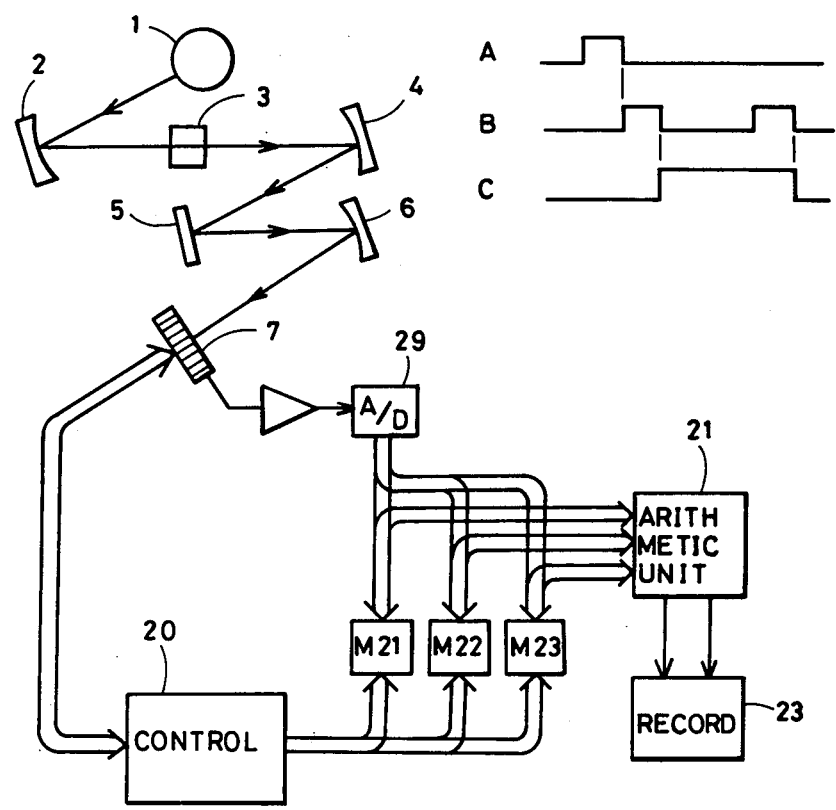
FIG. 5
FIG. 6
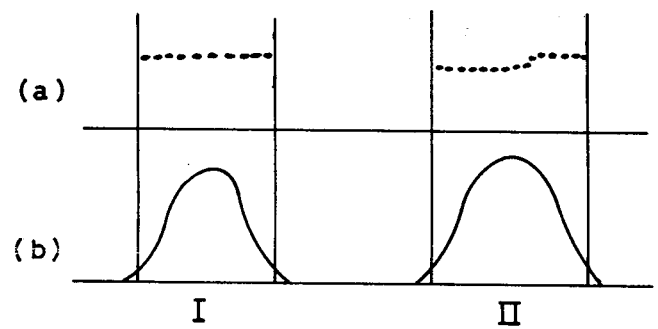

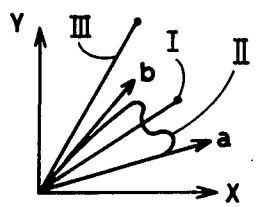
FIG. 7
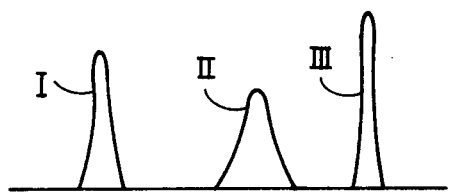
FIG. 8
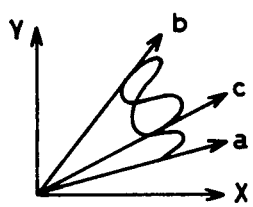
FIG. 9
FIG. 11
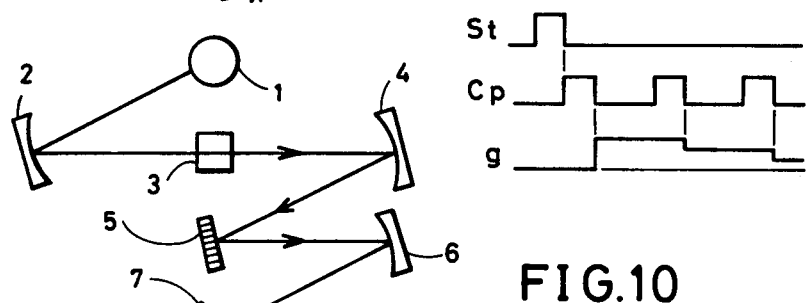
FIG. 10
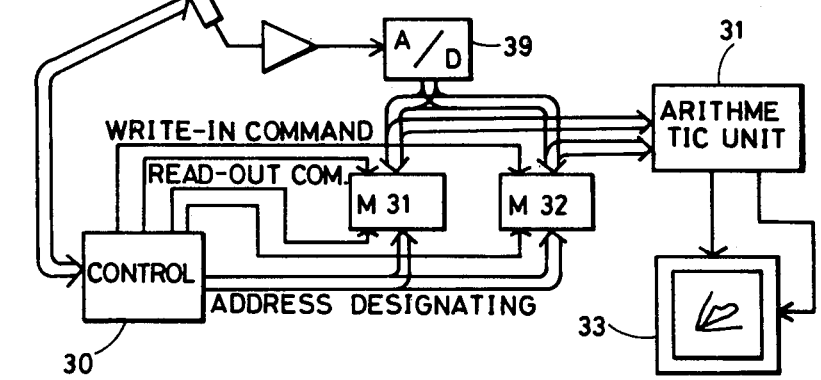

DETECTOR FOR CHROMATOGRAPHS

BACKGROUND OF THE INVENTION

This invention relates to detectors for use in chromatographs.

In analytical procedures where a spectrophotometer is employed in a detection system for liquid chromatographs, a method has been proposed to employ a spectroscope to measure light of a predetermined wavelength having an absorption peak with respect to sample components. In this method where absorbancy of light at a single wavelength alone is measured, the signal-to-noise (S/N) ratio is low, and in order to enhance the detector sensitivity it is required to intensify the light source and enlarge the spectral slit width. However, intensity of the light source is limited by available light sources. Another difficulty is that enlarging the slit width will cause the relationship of absorbancy to sample concentration to deviate from a straight line, so that quantitative accuracy will suffer. A primary object of this invention is to avoid the problems of light source intensity and large slit width.

In conventional recording of chromatograph detector outputs, one is not readily certain whether a recorded peak is due to a single component completely eluted or due to plural individual peaks separated incompletely. This uncertainty cannot be avoided by using a single detecting signal for providing a chromatogram.

One way to resolve this problem is to use plural detecting means to record plural chromatograms. Even with this method, however, it is still difficult to correctly interpret the resulting chromatogram. Observed peaks cannot be judged at a glance as to whether they represent incompletely separated components.

In techniques using plural detecting means, it is noted that the overall sensitivity depends upon the respective absorption of different components which inherently differ from each other. Accordingly, with reference to an observed peak on a chromatogram obtained from plural outputs of plural detecting means, a ratio among the respective detector outputs at an identical time which results in a constant value during the time period of the peak from the peak rise to its fall is due to a single component. In contrast, if the peak is due to plural component peaks superimposed, the ratio will vary with time depending upon their progressive rate of separation.

Another object of this invention is to provide a technique to provide that observed peaks can be judged at a glance as to whether they represent incompletely separated components. With the technique of the invention, at selected times a ratio among the respective detection outputs is obtained and a peak is judged to be related to a single component if a rectangular curve is traced; or the same peak is judged to be resulting from plural incompletely separated components if a curved curve is traced.

Plural detecting means may be optionally selected. The spectrophotometer for measuring absorbancy of light of plural wavelengths can be utilized in accordance with this invention. As such, a single apparatus is able to give plural detection signals representing spectral absorbancy and such absorbance signals provide very useful information about the identity of sample components.

As stated above, when plural detecting means are employed as detectors for a chromatograph, analytical information obtained depends upon differences in the sensitivity of the detector components in addition to the holding time with respect to separated sample components. It is exceedingly advantageous to distinguish component materials or peaks having components separated insufficiently.

The employment of plural detectors for use in a chromatograph has a problem, however, in that subsequent analytical processing of data is troublesome because there is such a large quantity of data. An object of this invention is to resolve this difficulty. In addition, plural detecting means are optionally selected. For instance, when a spectrophotomeric method is applied to predetermined light of plural wavelengths, detection data can be obtained for each selected wavelength. Thereby similar results as obtained in cases of employing plural detecting means can be obtained despite employing only one spectrophotometer.

For instance, when spectrophotometric analysis is applied continuously to chromatograph column effluent, records of change in absorption coefficient are obtained for light in several selected wavelengths. In these records, the set of absorbancy values for light in each wavelength at a given time can be regarded as one vector. This vector is recorded and its variation with time is investigated. Thereby provision of information from the recorded data is made much easier rather than by recording a change in many absorbancies. When considering a chromatogram as one traced pattern, its pattern recognition can be made easily.

Now, one peak of a chromatogram is taken into consideration, and this peak is assumed to be one wherein a component is completely separated. Since its separation is complete, this peak represents a change in concentration of a single component, and the value of absorbancy for light in predetermined plural wavelengths varies with the change in concentration from the peak rise to its fall; but a ratio of absorbancy among said wavelengths remains unchanged.

That is to say, a vector comprising vector components having absorbancy for each wavelength extends in its absolute value gradually from zero to an extreme maximum and thereafter becomes zero again, but the vector direction does not vary, and vector traces of change with time are expressed by a straight line in a direction, whose length alone is extended or contracted with time. The straight line vector represents a single sample component fully eluted.

Conversely, when vector tips of absorbancy depict a curved locus with time, it can be judged that a shown peak does not represent a single component. When taking two wavelengths, the vector is two-dimensional, and its change with time can be recorded by means of an X-Y recorder. FIG. 7 shows records of vector changes in this case, and FIG. 8 shows an ordinary chromatogram, whose three peaks I, II and III correspond to vector records I, II and III respectively in FIG. 7. The peaks I and III are the ones having one component completely separated, and their vector records are of one straight line as shown by I and III respectively in FIG. 7. Since the components representing these respective peaks are dissimilar, the ratios of absorbancy for two wavelengths differs. Accordingly I and III in FIG. 7 are shown with straight lines in different directions.

The peak II is one where components are not separated completely, and its vector record becomes a curved line as shown by II in FIG. 7. This peak comprises two components, and its vector components are considered to be tangents a and b at the origin of said curve. Although the peaks of these components are superimposed, the times when these peaks appear are offset from each other, and at the peak rise and the peak fall a single component exists. During development of the peak, two components exist in a mixed state while changing the ratio of concentration. Therefore, its vector record becomes a curve, for instance, that shifts gradually from vector a to vector b.

When one peak is formed by superposition of three component peaks, its vector record has three protrusions as shown in FIG. 9. In this case, components a, b and c constitute this peak, and this figure shows that elution is performed in a sequence of a, b, and c, or c, b, and a.

When detecting means of a number n where n>2 are used, the vector record has to be made in such a manner that only two data are taken from n data and are recorded on a X-Y recorder as two-dimensional, and a maximum number $(n-1)$ of two-data sets are processed for recording.

SUMMARY OF THE INVENTION

Accordingly, it is a primary object of the invention to provide a detector for use in a chromatograph having its signal-to-noise ratio enhanced and its sensitivity improved as compared with conventional detectors using a single wavelength. In accordance with the invention, wavelength scanning is conducted by means of a spectrophotometer to measure absorbancy for each of plural wavelengths and to integrate the measured absorbancies throughout the full range of the plural wavelengths, thereby to obtain a chromatogram.

It is a second object of this invention to provide a detector for use in chromatographs having plural detecting means, wherein detection data are analyzed and recorded, and whereby it can be judged at a glance if a shown peak represents a single component or plural components.

BRIEF DESCRIPTION OF THE DRAWINGS

The foregoing and other objects, features and advantages of this invention will be apparent from the following more particular description of preferred embodiments as illustrated in the accompanying drawings in which reference characters refer to the same parts throughout the various views.

FIG. 1 is an explanatory graph illustrating a principle underlying the method of this invention;

FIG. 2 is a block diagram showing an embodiment of the invention;

FIG. 3 is an example of chromatogram obtained from the embodiment shown in FIG. 2;

FIG. 4 is a block diagram showing another embodiment of the invention;

FIG. 5 is a time chart for operation of the embodiment shown in FIG. 4;

FIG. 6 is an example of a ratio record obtained from the embodiment shown in FIG. 4;

FIGS. 7 and 9 are examples of vector records obtained from the embodiment of the invention shown in FIG. 10;

FIG. 8 is an example of a chromatogram obtained from the embodiment shown in FIG. 10;

FIG. 10 is a block diagram showing still another embodiment of the invention; and, FIG. 11 is a time chart for operation of the embodiment shown in FIG. 10.

DETAILED DESCRIPTION OF THE INVENTION

A first embodiment of this invention is referred to in FIGS. 1-3. FIG. 1 is a graph wherein the abscissa indicates wavelength and the ordinate indicates transmitted light intensity. Symbol "C" denotes a curve of transmitted light intensity for the case of carrier fluid alone. Symbol "S" denotes a curve of transmitted light intensity for the case where a sample is eluted. The sloped line portion indicates absorption by a sample component.

Heretofore, a chromatograph column effluent absorbancy is measured with reference to absorption a at a position of wavelength $\lambda_o$ within an absorption region to describe a chromatogram.

According to this embodiment, a scanning range of $\lambda_1$ to $\lambda_2$ is set within the absorption region of a sample, and absorbancy for each wavelength within said range is measured and then integrated, so that noises in measurement of a single wavelength are mutually balanced to the others and then averaged to greatly improve its detection S/N ratio and sensitivity. In this way, a detector for use in a chromatograph having a high S/N ratio and high sensitivity can be obtained without the need for intensifying light sources or enlarging spectral slit widths.

FIG. 2 is a block diagram showing one embodiment of this invention. Element 1 is a light source, 2 is a concave mirror, 3 is a flow cell through which chromatograph column effluent is passed. Element 4 is a concave mirror for collimation, 5 is a diffraction grating, and 6 is a concave mirror. Light from source 1 is directed into flow cell 3 by means of concave mirror 2, and is collimated into parallel beams by means of collimator mirror 4 and then directed onto diffraction grating 5. The diffracted light is transformed into a spectrum image formed on the sensing surface of a photodiode array 7 by means of concave mirror 6. Outputs of the photodiode array 7 are amplified, converted by a logarithm converter 8, inputted into an A-D converter 9, and transformed in digital signals.

Element 10 is a control device which performs the following operations. Two outermost wavelengths $\lambda_1$ and $\lambda_2$ in a proper range (see FIG. 1) of an absorptive spectrum about a single component to be detected are preset in control device 10. Carrier fluid alone is made to flow in flow cell 3. When a command for base line set is given to control device 10, this device operates to have outputs of the unit elements of photodiode array 7 sequentially read out signals, corresponding to wavelengths $\lambda_1$ to $\lambda_2$ in the preset range, the signal outputs are transformed into digital values by an A-D converter 9 and subsequently stored respectively in addresses of a memory M1 corresponding to the wavelengths scanned. The inputted data of memory M1 are defined conveniently as I ($\lambda$, t1).

After base line readings are obtained, a sample is introduced into a chromatograph column and a command for detection is given to control device 10. As a result, control device 10 operates at constant intervals to have outputs of the respective elements of photodiode array 7 to be read, corresponding to wavelengths ranging from $\lambda_1$ to $\lambda_2$ in the preset range. Scanned outputs are A-D converted and stored respectively in addresses of a memory M2 corresponding to the wavelengths scanned. The data of memory M2 are defined as I(λ, ti), wherein i is an integer more than 2. In the initial operation, the content of memory M2 is I(λ, t2). When inputting of the data I(λ, ti) to memory M2 is terminated, data of the respective addresses of both memories M1 and M2, corresponding to identical wavelengths are sequentially read and transferred to a subtraction circuit 11. From the subtraction circuit the signals flow to an integration circuit 12 for integration throughout the range of wavelengths λ1 to λ2. Namely, an arithmetic operation is conducted according to a formula expressed by $$Ai = \sum_{\lambda_1}^{\lambda_2} \{I(\lambda, t1) - I(\lambda, ti)\} \quad (1)$$

The above arithmetic result is measured one at a time ti. Time ti is given at every constant interval, but a point t2 is a starting point for the detecting operation. The above arithmetic operation is performed at each time ti. The time period required for the above operation is relatively short, compared with the time interval before the next operation. In short, the operation according to formula (1) is conducted by starting of detecting operation, and repeated at constant intervals. A series of the resulting data Ai (i=2, 3, . . . ) are transferred to a recorder 13 where chromatogram as shown in FIG. 3 can be described.

Since data I(λ, t1) are logarithm converted values of transmitted light intensity for the case of carrier fluid alone, and data I(λ, ti) are the data for the chromatograph column effluent after introduction of a sample, a formula I(λ, t1)−I(λ, ti) indicates absorbancy of the chromatograph column effluent for each wavelength. The obtained absorbancy is integrated throughout wavelengths λ1-λ2, so that value Ai gives absorbancy of the chromatograph column effluent in a range of wavelengths λ1-λ2 at a time ti, and recorder 13 displays time variation of the absorbancy. Photodiode arrays having 200-500 unit elements are used. When a unit element is assigned to every wavelength difference of 1 nm, photodiode arrays of about 500 elements can cover a wavelength range of 200-700 nm.

Individual array elements of the photodiode array have corresponding addresses in both memories M1 and M2, and the photodiode array is scanned from end to end, without the need for presetting a scanning wavelength range λ1-λ2.

In order that the requisite portion of an absorption spectrum of a sample component be detected on photodiode array 7 diffraction grating 5 and photodiode array 7 may be so arranged that the first unit element of said array should correspond to address No. 1 of both memories M1 and M2. The second array element corresponds to memory address No. 2, and so on.

In the foregoing embodiment, a microprocessor is used for control device 10. Subtraction circuit 11 and integration circuit 12 are implemented by using the microprocessor and memory addresses of its main memory.

A conventional spectrophotometer by itself does not accomplish wavelength scanning. To do so, a system is adopted for scanning spectrum image faces on an array of photodiodes.

Another system is also feasible with the invention. This system comprises driving a diffraction grating to conduct wavelength scanning, detecting direction of the grating to obtain data of wavelengths and inputting light measurement data into memories by using the obtained data as address designating signals. Further, in the aforesaid embodiment, memory M1 is used for storing absorption spectrum data for carrier fluid alone in advance.

According to another embodiment of the invention, two light sources are employed, and measurements may be repeated to provide integrating in a predetermined wavelength range either ratios or logarithm differences of cell transmitted light for carrier fluid alone.

In accordance with this invention, a detector for use in a chromatograph records absorbancy at plural wavelengths, and integrates absorbancy throughout a wide absorption range of the absorption spectrum of the sample component to be detected. Absorbancy values at many wavelength points are added to increase detection outputs, whereby random noises at respective wavelength points are mutually balanced and averaged to improve a detection S/N ratio, to bring about a high gain in light measuring circuits, and to enhance overall detection sensitivity.

A second embodiment of this invention is described with reference to FIGS. 4-6. FIG. 4 is a block diagram showing the arrangement of elements in the embodiment. As in the first embodiment, a spectrum image is formed on photodiode array 7 by means of concave mirror 6. A control circuit 20 performs three kinds of control operations by which data are read out from photodiode array 7 and stored in memories. The data in the memories are read out and arithmetically processed; and the processed data are recorded. As an example, an analysis is explained for cases where five distinct wavelengths λ1-λ5 are measured.

Control circuit 20 includes a clock pulse generator and a counter. Reading out of data from photodiode array 7 begins with rise of a start pulse A shown in FIG. 5. Data from one element of photodiode array 7 is read for a rise period of a pulse C, namely from fall of a clock pulse B to fall of a subsequent pulse B, as referred to in FIG. 5. The read data are stored in either of memories M21, M22 and M23 after having been processed in an A-D converter and logarithm conversion circuit 29. The counter begins to operate with rise of a start pulse A. Elements of photodiode array 7 are designated sequentially according to their count data, and photodiode array 7 is repeatedly scanned. Scanning of array 7 is conducted at first when flow cell 3 is vacant. The data read from individual elements of array 7 are stored in corresponding addresses of memory M21 through circuit 29. In this way, the data of memory M21 are data relating to absorption spectrum of vacant flow cell 3.

Next, where carrier alone is passed to flow cell 3, the same operation as the foregoing is conducted, and the data are stored in memory M22. In this way, memory M22 holds spectrum data having absorbancy of flow cell 3 and carrier added.

After these two kinds of data are stored in respective memories M21 and M22, the sample is caused to flow through the flow cell 3, and the scanning of photodiode array 7 is repeated and the read data are stored in memory M23 through circuit 29. The stored data are rewritten by every scanning of array 7. The required period for a scanning of photodiode array 7 is relatively very short compared with a period of continuity of chromatogram peaks. For this reason, the contents of memory M23 correspond to an absorptive spectrum of chromatograph column effluent at sequential times.

Control circuit 20 accomplishes, in addition to the foregoing operations, the following operation. This operation is conducted during the period from a scanning of photodiode array 7 to its next scanning. An arithmetic operation is conducted, for instance, as to five distinct wavelengths $\lambda_1$–$\lambda_5$. Respective five wavelength data are read out from the corresponding addresses of memories M21, M22 and M23 for wavelengths $\lambda_1$–$\lambda_5$, as a group of five data, and can be regarded as a vector having five vector components. A group of five data read from memory M21 provides a vector indicating absorbancy characteristics of vacant flow cell 3, and symbolized A. Another group of five data read from memory M22 provides a vector indicating absorbancy characteristics of flow cell 3 and carrier fluid added, and symbolized B. The still other group of five data read from memory M23 provides a vector indicating absorbancy characteristics of chromatograph column effluent in the flow cell at a point in time (though in the narrow sense there exists a width of time required for a scanning of photodiodes array, the width can be regarded a point in time as compared to the speed of the chromatogram), and symbolized Ci, wherein its suffix i expresses a point of individual times. This vector includes characteristics of a sample component so long as it is eluted.

Control circuit 20 operates to have the aforesaid three kinds of vector data at a point of time i (i=1, 2 ...) read out and a calculation Di=B−Ci (Vector subtraction) performed at every point in time. The vectors underlying the vector Di are subtracted absorbancy of flow cell and carrier fluid added. Absorbancy of a sample vector component with respect to light in vector component wavelengths $\lambda_1$–$\lambda_5$ at a time ti are designated di1−di5.

Control circuit 20 also controls calculating an absolute value of vector Di from its vector components according to an expression given by $|Di| = \sqrt{di1^2 + \ldots + di5^2}$. This absolute value is in proportion to concentration of a sample component eluted from the chromatograph column. In addition, a ratio among the respective vector components of vector Di indicates a sample component.

An important judgment to be made is whether or not a chromatogram peak is indicative of a single component or plural components inadequately separated. For this purpose, control circuit 20 causes to be calculated a ratio dij/|Di| (j=1, 2, ... 5) of the respective vector components di1−di5 of vector Di to the absolute value of vector Di, said ratio being a direction cosine with respect to direction of the respective vector components of vector Di. When a chromatogram peak represents a single sample component, the vector ratio indicates a constant irrespective of times so long as the peak is continued. Block 21 in FIG. 4 is an arithmetic circuit for the foregoing calculations at every time when photodiode array 7 is scanned (proper skipping unlike every scanning time is permissible), so that given ratios of dij/|Di| are plotted on a recorder 23.

In this example, five values of dij/|Di| can be given, but one among them may be properly selected. FIG. 6(a) indicates graphically plotted examples of the resulting records from recorder 23, wherein the abscissa denotes time i and the ordinate denotes values dij/|Di|. FIG. 6(b) indicates ordinary chromatogram peaks corresponding to the records of FIG. 6(a), said peaks being obtained by recording of value Di. In the figure, peak I represents a single component, and the plot of value dij/|Di| is a dotted straight line. Another peak II is a single peak on chromatogram, but has two sample component peaks superposed with offset of times. In FIG. 6(a), the plot of vector ratios is curved indicating incomplete separation.

Upon obtaining the object record from vector components in number n, a ratio of two vector components may be measured as to a pair number (n−1), but it will then happen to have a small value of its denominator, so that the value to be recorded is too large to cover a determined range. The vector ratio approach is free from this scaling problem because a direction cosine to respective vector component directions covers a range of 0 to 1.

A third embodiment of this invention is described by referring to FIGS. 7–11. Also in this embodiment, absorption spectrum images of chromatograph column effluent are formed on photodiode array 7 by means of concave mirror 6. A control device 30 performs operations comprising designating sequentially individual elements of photodiode array 7, reading measured light outputs therefrom, converting the same into digital data by means of an A-D converter 39, and writing the resulting data into addresses of a memory M31 or M32, corresponding to the wavelengths. Control device 30 also controls operations involving reading contents of memories M31 and M32, and performing required arithmetic operations by means of an arithmetic circuit 31. Thereby a locus of vector tips can be recorded on an X-Y recorder or a plotter 33.

Control unit 30 produces clock pulses Cp as shown in FIG. 11 by means of a generator built therein, and instructs for an operation of reading outputs of individual elements of photodiode array 7 at rise of a start pulse St as shown in FIG. 11. In this case, clock pulses are counted and then the output of the i-th element of photodiode array 7 is read out corresponding to a count number i, and this reading is carried out between fall of the i-th clock and fall of the (i+1)th clock pulse, thus photodiode array 7 is scanned repeatedly. Clock counter number i is a datum for designating an element of photodiode array 7, and accordingly should correspond to a wavelength. Symbol "g" in FIG. 11 shows a change with time in the analogue data thus read from photodiode array 7, and with respect to a time of scanning its graph corresponds to a spectral image during its scanning period. Control device 30 commands A-D and logarithm conversion of this analogue data and writing of the resulting data to an address of memory M31 or M32 corresponding to counter number i. Whether data is written to M31 or to M32 is determined by a program and is carried out as follows:

Firstly, photodiode array 7 is scanned with carrier fluid alone flowing through flow cell 3, and the resulting data at this time are written to memory M31. Next, the sample is made to flow through flow cell 3, during which time the data from photodiode array 7 are written to memory M32. This writing to memory M32 is performed in such a manner that new data are cumulatively rewritten for every subsequent scanning. Scanning of photodiode array 7 is repeated at a considerably high speed, compared with the change with time in chromatogram, and accordingly the data of memory M32 correspond to absorption spectrum of chromatograph column effluent to provide a smooth continuous chromatogram.

Control device 30 controls the recording of vectors in the following manner. The data in the respective addresses of memories M31 and M32 corresponding to two wavelengths $\lambda_1$ and $\lambda_2$ are read out at an appropriate time interval. The data written in memory M31 are converted to logarithm values of light transmittance for carrier fluid alone, and the above data (converted logarithm values) for said carrier fluid in respective wavelengths $\lambda_1$ and $\lambda_2$. That is, the data read from memory M31 are defined as A ($\lambda_1$) and A ($\lambda_2$).

Furthermore, the data in memory M32 are converted logarithm values of light transmittance for a mixed fluid of carrier fluid with a sample component, and the data read from memory M32 are defined as C ($\lambda_1$) and C ($\lambda_2$). These data are sent to arithmetic circuit 31, where expressions A ($\lambda_1$) − C ($\lambda_1$) = S ($\lambda_1$) and A ($\lambda_2$) − C ($\lambda_2$) = S ($\lambda_2$) are calculated. Then S ($\lambda_1$) and S ($\lambda_2$) are inputted into X-Y recorder or plotter 33, respectively as X- and Y-axis values, thereby one coordinate point is recorded. That is, S ($\lambda_1$) and S ($\lambda_2$) become absorbancy for the sample component in wavelengths $\lambda_1$ and $\lambda_2$. The above operation is carried out between the end of one scanning of photodiode array 7 and start of the next scanning. Accordingly, this operation is conducted at a relative instant in time as compared with the length in time to obtain a chromatogram. By repeating this operation at appropriate time intervals, the record of change with time in vectors derived from two components of absorbancy values for two wavelengths is obtained, and this record is expressed as a pattern as exemplified in FIGS. 7 and 9.

The above mentioned combination of wavelengths $\lambda_1$ and $\lambda_2$ may be fixed over all peaks in the chromatogram and may be changed for individual peaks in the chromatogram provided that recording of change in vectors is carried out individually for every peak.

In the record of change in vectors (FIGS. 7 and 9) obtained according to the invention, the direction of vectors indicates the sample component and the length indicates the concentration of the component. Therefore this record provides both qualitative and quantitative information, and similar samples produce similar records so that identification of samples can be made simply by examining whether or not two records are coincident with each other when superposed.

Furthermore, as described above when separation is complete, the locus of change in the vectors is a straight line. However, if the locus depicts a curvy line, the separation can be judged to be incomplete. When vector records from plural components are superposed, some useful information can be obtained about the components. In addition, a locus recording of change in vectors does not contain a time component as does a usual chromatogram. The vector pattern is a simplification of a chromatogram pattern. It is easy to computerize the operation of comparing two records to decide whether the two records are similar or not, or whether separation of components about a peak is complete or incomplete.

While the invention has been particularly shown and described with reference to the preferred embodiments thereof, it will be understood by those skilled in the art that various alterations in forms and detail may be made therein without departing from the spirit and scope of the invention.

The embodiments of the invention in which an exclusive property or privilege is claimed are defined as follows:

1. Apparatus for use in combination with a chromatograph column comprising:
    means for detecting the degree of transmission of light through a chromatograph column for a plurality of selected wavelengths (j) and for generating signals in accordance with said detected transmission for said selected wavelengths;
    computing means which computes a ratio with respect to at least one of said selected wavelengths, said ratio having as its numerator a value indicative of the signal generated by said detecting means for one of said selected wavelengths and having as its denominator a value corresponding to the square root of a summation of the algebraic squares of values indicative of the signals generated by said detecting means with respect to each of said selected wavelengths; and,
    means connected said detecting means to said computing means.

2. The apparatus of claim 1, wherein said detecting means detects the transmission of light through a plurality of successive time intervals (i) and generates a signal dij in accordance with said detected transmission for said selected wavelengths (j) for each time interval (i), and wherein said computing means computes the ratio $$d_{ij}/|D_i| \, (j=1,2\ldots n)$$

where $$|D_i| = \sqrt{\frac{2}{d_{i_1}} + \frac{2}{d_{i_2}} + \cdots \frac{2}{d_{i_n}}}$$

and where
   n = an integer indicative of the total number of selected wavelengths;
   j = a selected wavelength, which varies from 1 to n;
   i = an integer number indicative of a time interval of interest; and,
   d = a measured signal for detected transmission for a selected wavelength and selected time interval.

3. The apparatus of claim 1 or claim 2, further comprising means for displaying values indicative of said ratio as said ratio is calculated for said selected wavelengths, said display means being connected to said computing means.

4. Apparatus for use in combination with a chromatograph column comprising:
    means for detecting during successive time intervals the degree of transmission of light through a chromatograph column for at least two selected wavelengths and for generating signals in accordance with said detected transmission for said selected wavelengths during each time interval;
    computing means for computing directional vector values with respect to each of said wavelengths in accordance with the incrementation of time through said time intervals;
    means connecting said computing means to said detecting means; and
    means for recording said directional vector values.

5. A method for obtaining information with respect to analysis involving a chromatograph column, said method including the steps of:
    detecting the degree of transmission of light through a chromatograph column for a plurality of selected wavelengths;

generating signals in accordance with said detected transmission for said selected wavelengths; and, computing a ratio with respect to at least one of said selected wavelengths, said ratio having as its numerator a value indicative of the signal generated by said detecting means for said one selected wavelength and having as its denominator a value corresponding to the squre root of a summation of the algebraic squares of values indicative of the signals generated by said detecting means with respect to each of said selected wavelengths.

6. The method of claim 5, wherein said step of detecting the degree of transmission of light for a plurality of selected wavelengths further involves the detection of the transmission of light through a plurality of successive time intervals for each selected wavelength, and wherein said step of generating signals includes the generation of a signal dij in accordance with said detected transmission for said selected wavelengths for each time interval, and wherein in said computing step said computing means computes the ratio $$dij/|Di| \, (j=1,2 \ldots n)$$

where $$|Di| = \sqrt{\frac{2}{di_1} + \frac{2}{di_2} + \ldots \frac{2}{di_n}}$$

and where
- n = an integer indicative of the total number of selected wavelengths;
- j = a selected wavelength, which varies from 1 to n;
- i = an integer number indicative of a time interval of interest; and,
- d = a measured signal for detected transmission for a selected wavelength and selected interval.

7. The method of claims 5 or 6, further comprising the step of displaying values indicative of said ratio as said ratio is calculated for said selected wavelengths.

* * * * *